US012584002B2

(12) United States Patent
Dowling

(10) Patent No.: US 12,584,002 B2

(45) **Date of Patent: *Mar. 24, 2026**

(54) VARIABLE-SIZE HYDROPHOBICALLY-MODIFIED POLYMERS

(71) Applicant: Medcura, Inc., Riverdale, MD (US)

(72) Inventor: Matthew Dowling, Riverdale, MD (US)

(73) Assignee: Medcura, Inc., Riverdale, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/122,208

(22) Filed: Mar. 16, 2023

(65) Prior Publication Data

US 2023/0323096 A1 Oct. 12, 2023

Related U.S. Application Data

(63) Continuation of application No. 17/568,790, filed on Jan. 5, 2022, now abandoned, which is a continuation (Continued)

(51) Int. Cl.

*A61L 15/28* (2006.01)
*A61L 15/26* (2006.01)

(Continued)

(52) U.S. Cl.

CPC ................ *C08L 5/08* (2013.01); *A61L 15/26* (2013.01); *A61L 15/28* (2013.01); *A61L 24/08* (2013.01); *C08B 37/003* (2013.01); *C08L 71/00* (2013.01)

(58) Field of Classification Search

CPC .. C08L 5/08; C08L 71/00; A61L 15/26; A61L 15/28; A61L 24/08; C08B 37/003

See application file for complete search history.

(56) References Cited

U.S. PATENT DOCUMENTS

| | | | |
|---|---|---|---|
| 2,651,629 | A | 9/1953 | White et al. |
| 6,517,678 | B1 | 2/2003 | Shannon et al. |

(Continued)

FOREIGN PATENT DOCUMENTS

| | | | |
|---|---|---|---|
| KR | 101106627 | B1 | 1/2012 |
| WO | 2018184021 | A1 | 10/2018 |
| WO | 2020181015 | A1 | 9/2020 |

OTHER PUBLICATIONS

Chiandotti et al., "Grafting of Chitosan with Fatty Acyl Derivatives", J. Braz. Chem. Soc., vol. 21, No. 10, 1910-1916, 2010. (Year: 2010).*

(Continued)

*Primary Examiner* — Jianfeng Song

(74) *Attorney, Agent, or Firm* — Morgan, Lewis & Bockius LLP

(57) ABSTRACT

In various aspects, the invention provides compositions of variable-length hydrophobically-modified polymers. These variable-length hydrophobes decorated along the hydrophilic polymer backbone provide advanced properties and allow for precise control over the behavior of the resulting amphiphilic polymer, including in aqueous solution. Such control allows for enhanced functionality of the amphiphilic polymer relative to standard single-length hydrophobe grafting designs, including for hemostasis.

7 Claims, 9 Drawing Sheets

Related U.S. Application Data of application No. 16/603,933, filed as application No. PCT/US2018/027637 on Apr. 13, 2018, now abandoned.

(60) Provisional application No. 62/484,985, filed on Apr. 13, 2017.

(51) Int. Cl.

| | |
|---|---|
| ***A61L 24/08*** | (2006.01) |
| ***C08B 37/08*** | (2006.01) |
| ***C08L 5/08*** | (2006.01) |
| ***C08L 71/00*** | (2006.01) |

(56) References Cited

U.S. PATENT DOCUMENTS

| | | | | |
|---|---|---|---|---|
| 6,699,499 | B1 | 3/2004 | Aneja et al. | |
| 8,664,199 | B2 | 3/2014 | Dowling et al. | |
| 8,668,899 | B2 | 3/2014 | Dowling et al. | |
| 8,858,883 | B2 | 10/2014 | Dowling et al. | |
| 8,932,560 | B2 | 1/2015 | Dowling et al. | |
| 9,066,885 | B2 | 6/2015 | Raghavan et al. | |
| 9,616,088 | B2 | 4/2017 | Diehn et al. | |
| 10,179,145 | B2 | 1/2019 | Dowling et al. | |
| 10,493,094 | B2 | 12/2019 | Diehn et al. | |
| 2007/0156084 | A1 | 7/2007 | Belhe et al. | |
| 2008/0064843 | A1 | 3/2008 | Daly | |
| 2008/0254104 | A1 | 10/2008 | Raghavan et al. | |
| 2010/0069536 | A1 | 3/2010 | Sau | |
| 2011/0280857 | A1* | 11/2011 | Dowling | A61L 26/0076 424/94.64 |
| 2012/0058970 | A1* | 3/2012 | Dowling | A61L 15/28 514/57 |
| 2012/0252703 | A1 | 10/2012 | Dowling et al. | |
| 2014/0314706 | A1* | 10/2014 | Diehn | A61K 38/39 424/78.37 |
| 2015/0151005 | A1 | 6/2015 | Bouchemal | |
| 2019/0159992 | A1 | 5/2019 | Dowling | |
| 2020/0046870 | A1 | 2/2020 | Dowling et al. | |
| 2020/0102446 | A1 | 4/2020 | Dowling | |

OTHER PUBLICATIONS

Li et al., "Aggregation of Hydrophobically Modified Chitosan in Solution and at the Air-Water Interface", Journal of Applied Polymer Science, vol. 102, Issue 2, 1968-1973, 2006. (Year: 2006).*

Abdelaal et al., "Modification of chitosan derivatives of environmental and biological interest: A green chemistry approach", International Journal of Biological Macromolecules 55 (2013) 231-239.

Hu, et al., "Self-aggregation and antibacterial activity of N-acylated chitosan", ScienceDirect, Polymer 48 (2007) 3098-3106.

* cited by examiner

Native Chitosan (0ᵗʰ Order)

hm-Chitosan (5 mol % C8 grafts) – Single Length Grafting (1ˢᵗ Order)

hm-Chitosan (2.5 mol % C8 grafts, 2.5% C16 graft) – Variable Length Grafting (2ⁿᵈ Order )

hm-Chitosan (2 mol % C8 grafts, 2 mol % C16 grafts, 1mol % C20 graft ) – Variable Length Grafting (3ʳᵈ Order)

hm-Chitosan (1.25 mol % C4 grafts, 1.25 mol % C8 grafts, 1.25 mol % C16 grafts, 1.25 mol % C20 graft ) – Variable Length Grafting (4ᵗʰ Order)

Figure 4

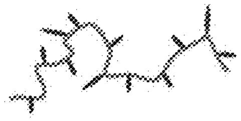

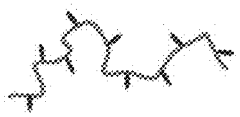

| Blood Fraction | 5M C12/1M C18 1.5wt% | 5M C12/1M C18 1.0wt% | 5M C12 1.0wt% |
|---|---|---|---|
| Whole Blood | GELS | GELS | GELS* |
| Blood Cells in Saline | GELS | GELS | Almost Gels |
| Blood Cells in HBSS | GELS | GELS | Almost Gels |
| Plasma | GELS | Almost Gels | Almost Gels |
| Saline Only | GELS | NO | NO |
| DI Water | NO | NO | NO |
| LYSED Whole Blood | GELS | NO | GELS* |
| LYSED Blood Cells in Saline | GELS | Almost Gels | Almost Gels |
| LYSED Blood Cells in HBSS | GELS | Almost Gels | Almost Gels |

* Does not gel immediately.

Figure 5

| | Hydrophobic Graft Design | | | | | | |
|---|---|---|---|---|---|---|---|
| Med MW Chitosan Variant | C8 | C10 | C12 | C14 | C16 | C18 | Gels blood |
| 1 | 1% | | | | | | No |
| 2 | | 1% | | | | | No |
| 3 | 5% | | | | | | No |
| 4 | | 5% | | | | | Yes |
| 5 | | | | | | 1.0% | Yes |
| 6 | | | | | 1.0% | | Yes |
| 7 | | | | 1.0% | | | Yes |
| 8 | | | 5.0% | | | | Yes |
| 9 | | 5.0% | | | | | Yes |
| 10 | 10% | | | | | | No |
| 11 | | | 2.5% | | | 1.0% | Yes |
| 12 | | 2.5% | | | | 1.0% | Yes |
| 13 | 10% | | | | | 1.0% | Yes |
| 14 | | | 2.5% | | 1.0% | | Yes |
| 15 | | 2.5% | | | 1.0% | | Yes |
| 17 | 10% | | | | 1.0% | | Yes |
| 18 | | | 2.5% | 1.0% | | | Yes |
| 19 | | 2.5% | | 1.0% | | | Yes |
| 20 | 10% | | | 1.0% | | | Yes |
| 21 | | | 5.0% | | | 1.0% | Yes |
| 22 | | 5.0% | | | | 1.0% | Yes |
| 23 | 10% | | | | | 1.0% | Yes |
| 24 | | | 5.0% | | 1.0% | | Yes |
| 25 | | 5.0% | | | 1.0% | | Yes |
| 26 | 10% | | | | 1.0% | | Yes |
| 27 | | | 5.0% | 1.0% | | | Yes |
| 28 | | 5.0% | | 1.0% | | | Yes |
| 29 | 10% | | | 1.0% | | | Yes |

Figure 6
All samples were dissolved in 0.067 M lactic acid solution.
| | | polymer:blood (v/v) ratio | | |
|---|---|---|---|---|
| Sample | Wt% | 1 to 1 | 1 to 0.5 | |
| 1 | 0.5 | flowable | Flowable | 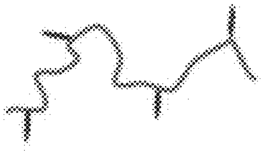 |
| 1 | 1.0 | Onset of gelation | Onset of gelation | |
| 2 | 0.5 | Flowable | Gel | 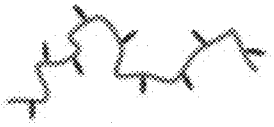 |
| 2 | 1.0 | flowable (with chunks) | Gel | |
| 3 | 0.5 | flowable | Flowable | 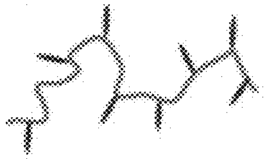 |
| 3 | 1.0 | Gel | Onset of gelation | |
| 4 | 0.5 | Weak gel | Strong gel | 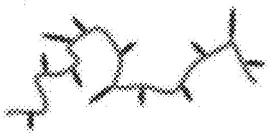 |
| 4 | 1.0 | Strong gel | Strong gel | |
| 5 | 0.5 | Gel | Strong gel | 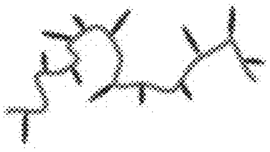 |
| 5 | 1.0 | gel | Gel | |
| Sample | Type |
|---|---|
| 1 | 1.0M C18 |
| 2 | 7.0M C12 |
| 3 | 2.5M C18 |
| 4 | 5.0M C12, 1.0M C18 |
| 5 | 5.0M C12, 2.5M C18 |

Legend
A – 1% C16
B – 1% C12
C – 1% C8
D – 1% C8, 1% C12, 1% C16
E – 20% C1, 1% C8, 1% C12, 1% C16
F – 40% C1, 1% C8, 1% C12, 1% C16
G – 60% C1, 1% C8, 1% C12, 1% C16

VARIABLE-SIZE HYDROPHOBICALLY-MODIFIED POLYMERS

PRIORITY

This application is a continuation of U.S. application Ser. No. 17/568,790, filed Jan. 5, 2022, which is a continuation of U.S. application Ser. No. 16/603,933, filed Oct. 9, 2019, which is a National Stage Entry of International Application No. PCT/US2018/027637, filed Apr. 13, 2018, which claims the benefit of U.S. Provisional Application No. 62/484,985, filed Apr. 13, 2017, the contents of which are hereby incorporated by reference in its entirety.

BACKGROUND

A vast array of hydrophobically-modified (hm) polymers has been created for various uses, such as: paints, industrial thickeners, drug delivery matrices, and hemostasis. The associations between the hydrophobic groups in water allow the polymers to self-assemble into 3-dimensional networks. These associations tend to thicken the resulting aqueous solutions created by these biopolymers.

However, hydrophobically-modified (hm) polymers generally have one length of hydrophobic grafts to the backbone of the polymer. Properties of polymers having variable graft structures, sizes, and densities have not been investigated.

SUMMARY OF THE INVENTION

In various aspects, the invention provides compositions of variable-length hydrophobically-modified polymers. These variable-length hydrophobes decorated along the hydrophilic polymer backbone provide advanced properties and allow for precise control over the behavior of the resulting amphiphilic polymer, including in aqueous solution. Such control allows for enhanced functionality of the amphiphilic polymer relative to standard single-length hydrophobe grafting designs.

In various embodiments, the invention provides a hm polymer or composition thereof, wherein the modified polymer has hydrophobic groups of at least two different sizes attached to the polymer backbone. These variable-length hm polymers are a new class of associating polymers, including for uses in water-treatment, cosmetics and personal care compositions, drug delivery, wound care, hemostasis, industrial paints/coatings, and other uses.

In some embodiments, the polymer or composition is a modified polymer that is amphiphilic. In some embodiments, the polymer is based on a polysaccharide backbone, such as chitosan, alginate, cellulosics, pectins, gellan gums, xanthan gums, dextrans, and hyaluronic acids, among others. In some embodiments, the polymer is a synthetic (i.e., non-natural) polymer, such as polyethylene glycol, polylactic acid, poly-glycolic acid, poly lactic co-glycolic acid, poly F-caprolactone, polyurethane, polymethylmethacrylate, and silicone, among others. In some embodiments, the polymer is chitosan.

The polymer may have from 2 to about 10 different hydrophobic groups, and optionally from 2 to about 5 different hydrophobic groups (e.g., 2, 3, or 4 different hydrophobic groups). The hydrophobic groups may be independently selected from linear, branched, or cyclic hydrocarbon groups. For example, the hydrophobic groups may include at least one saturated hydrocarbon, which is optionally an acyl group (e.g., fatty aldehyde or fatty acid anhydride).

In some embodiments, the polymer has at least one or at least two of:

(a) a C1 to C5 hydrocarbon group, which is optionally substituted by non-hydrocarbon moieties;

(b) a C6 to C12 hydrocarbon group, which is optionally substituted with non-hydrocarbon moieties;

(c) a C13 to C28 hydrocarbon group, which is optionally substituted with non-hydrocarbon moieties;

(d) a hydrophobic group having a size greater than C28, which is optionally substituted with non-hydrocarbon moieties. Non-hydrocarbon moieties include heteroatoms or groups comprising heteroatoms such as O, N, S, or halogen.

The polymer composition may be formulated as a solid, liquid, gel, foam, or putty. For example, the polymer may be a solid, which may be lyophilized or may be a dehydrated solution or dehydrated foam. In some embodiments, the polymer is formulated with one or more solvents. The solvents may comprise water. In some embodiments, the solvent comprises an industrial solvent, which may be an organic solvent. In some embodiments, the solvent is paint or industrial coating.

In some embodiments, the modified polymer is present at 0.1 to about 5% by weight in the composition, or in some embodiments, from 0.5 to 2.0% (e.g., about 0.5%, about 1.0%, 1.5%, or about 2%). In some embodiments, the polymer is formulated with at least one synthetic polymer. Exemplary synthetic polymers include polythene, polystyrene, polyacrylate, polyamide, polyester, polyurethane, polysulfide, and polycarbonate. In some embodiments, the synthetic polymer is polyvinyl alcohol.

The modified polymer may provide anti-bacterial and/or anti-fungal properties, which is desirable for many types of garments and fabrics, as well as cosmetic and personal care composition.

In some embodiments, the composition is a hemostatic device or dressing for bleeding control. There are a myriad of material characteristics that are desired for a well-functioning hemostatic material. For example, the material should be easy to apply (ideally flowable to conform to surfaces, cavities, and/or small areas), able to create a rapid seal when in contact with bleeding tissue, retain its mechanical integrity in the face of high pressure bloodflow, be easy to remove, and be safely bioresorbable if left inside the body after use. The present application provides a framework to create specific hydrophobic designs that employ multiple different grafting lengths and density of hydrophobic groups to achieve optimized properties in flowability, tissue adhesion, cohesion, biodegradation, and removability.

In some embodiments, the modified polymer (e.g., chitosan or other polymer disclosed herein) has both C8 and C18 acyl groups covalently attached to the backbone of the biopolymer, which is both adhesive to tissues, due to the C8 groups, and also cohesive under exudate flow, due the C18 groups. The C8 groups are fluid at room and body temperature, allowing the polymer to spread onto the cell surfaces more effectively, whereas the C18's on neighboring polymer chains hold the polymer molecules together strongly even in the presence of high exudate or blood flow. These embodiments can thus balance adhesive and cohesive properties.

Alternatively, or in addition, incorporation of small hydrophobic groups, such as C1 to C4 acyl chains, allows the chitosan to degrade more predictably from lysozyme activity in the body. This is very important for creating a material which can be left inside the body after treatment of the wound. More specifically, hydrophobic groups below the length of C6 do not contribute towards improved hemostatic effect. However, hydrophobic modification in the range of C1 to C6 allow for a framework to optimize the degradation of the material inside the body via lysozymes. Particularly in the case of surgical-use hemostats, it is ideal for the hemostatic biomaterial to degrade quickly after achieving hemostasis.

In some aspects, the invention provides a method for treating a wound, comprising, applying the polymer or composition with hemostatic properties to a bleeding wound. In some embodiments, the wound has high exudate or blood flow. In some embodiments, the polymer composition provides advantages in tissue adhesion as well as material cohesion (for creating a barrier even with high blood flow). In some embodiments, the material degrades in the body within two months, within one month, within two weeks, or within one week, or with about 2 days. In some embodiments, the material is mechanically removable from the wound without damaging the underlying tissue. In various embodiments, the modified polymer (in the amount employed) is soluble in aqueous environment.

A hydrophobically-modified (hm) biopolymer material for incorporation into aqueous or organic solutions or suspensions can be based on a solution of the hm-biopolymer that is about 0.1% to about 5.0% by weight relative to the total weight of the composition, or in some embodiments, about 0.5% to about 4%, or about 0.5% to about 3% of the total weight of the composition, or about 0.5% to about 2% of the total weight of the composition.

Hydrophobic moieties can be independently selected from saturated hydrocarbons (e.g., alkanes) and unsaturated hydrocarbons (e.g., alkenes, alkynes), which may be linear, branched or cyclic. In some embodiments, the hydrophobic moieties include aromatic hydrocarbons. In some embodiments, the hydrophobic moieties are fatty acids conjugated to polymer functional groups, including amines or hydroxyl groups. An exemplary conjugation chemistry is a fatty acid anhydride.

Other aspects and embodiments of the invention will be apparent from the following detailed description.

DESCRIPTION OF THE FIGURES

FIG. 4 shows blood gelation experiments. A 1.0 mL sample of each hm-chitosan solution (2 wt %) was mixed with 0.5 mL of each blood fraction and vortexed thoroughly. Modified polymer compositions include 5 mol % C12, 1 mol % C18, 1.5 wt %; 5 mol % C12, 1 mol % C18, 1.0 wt %; and 5 mol % C12, 1.0 wt %.

FIG. 5 shows the results of blood gelling capability of various hydrophobic grafting designs along chitosan backbone. All hydrophobic design grafts are attached to a medium molecular weight chitosan (Primex hqg 400). Solutions of hm-chitosans were 1.5 wt % of polymer dissolved in 0.2 M acetic acid in water. Several 2nd, 3rd and 4th order grafting designs are described via % mol of amines along the chitosan backbone. Gelling is defined as an ability for a mixture of polymer and blood (citrated bovine blood (Lampire)) as a ratio of 2:1 (v/v) to hold its own weight upon vial inversion.

FIG. 6 shows blood gelation experiments with 5 different hm-chitosan constructs at different wt % (0.5 and 1.0 wt %) and at different ratios with blood. Samples 4 and 5, incorporating C12 and C18 hydrophobic grafts, showed the strongest gelation properties.

DETAILED DESCRIPTION OF THE INVENTION

Figure 1:
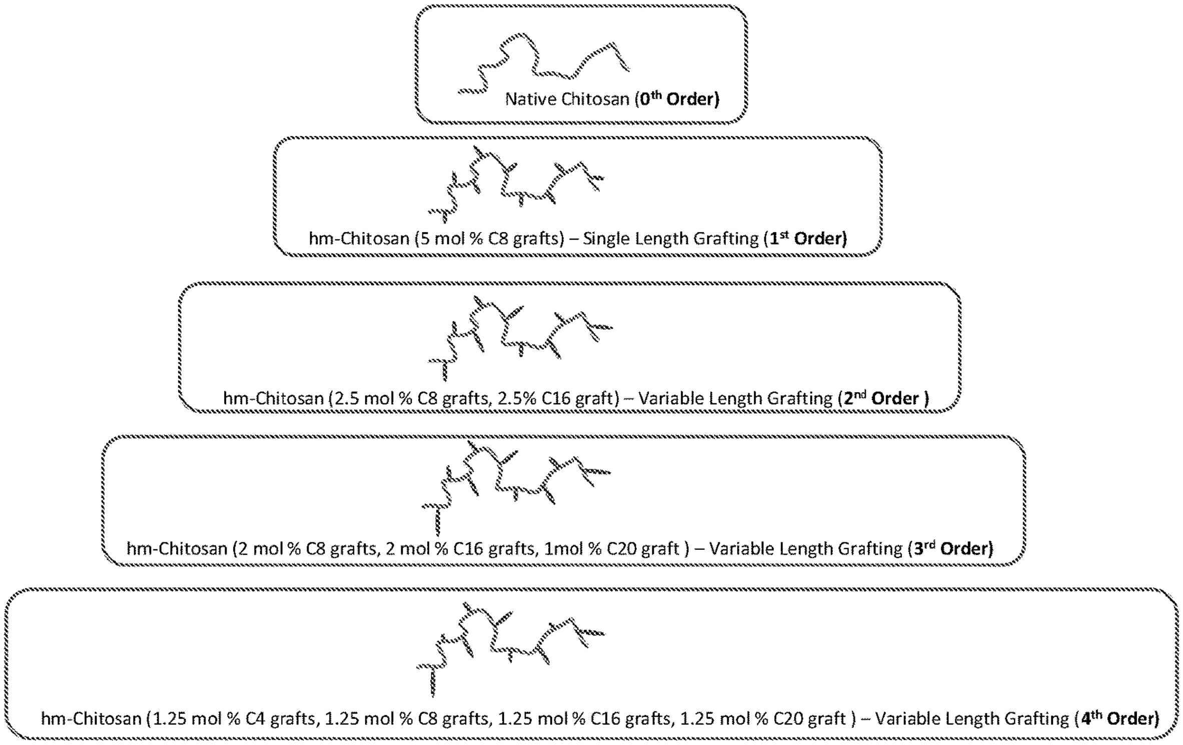
FIG. 1 illustrates variable-sized hydrophobically-modified (hm) chitosans, including from the top: native chitosan (zero-order (0th Order) hm-chitosan), chitosan having C8 hydrophobes at a grafting density of 5 mol % of available amines along the backbone (a first-order (1st Order) hm-chitosan), and second-order (2nd Order), third-order (3rd Order) and fourth-order (4th Order) hm-chitosans, meaning that two, three and four types of hydrophobic species, of differing sizes and structures, are found along the backbone of the polymer.

In various aspects, the invention provides compositions of variable-length hydrophobically-modified polymers for use in applications such as wound treatment, drug delivery, cosmetics, textiles, and others. Known hydrophobically-modified polymers generally have one length of hydrophobic grafts to the backbone of the polymer, albeit at various grafting densities. In accordance with embodiments of the present invention, variable-length hydrophobes decorated along the hydrophilic polymer backbone allow for precise control over the behavior of the resulting amphiphilic polymer. Such control allows for enhanced functionality of the amphiphilic polymer relative to standard single-length hydrophobe grafting designs. The enhanced functionalities can result from novel three dimensional structures created by these polymers.

In various embodiments, the invention provides a hydrophobically-modified polymer or composition thereof, wherein the modified polymer has hydrophobic groups of at least two different sizes attached to the polymer backbone. These variable-length hydrophobically-modified polymers are a new class of associating polymers. These polymers provide a greater level of control over how these polymers interact with themselves and with other entities in an aqueous or organic environment. This results in a new regime of functionality which may have uses in water-treatment, cosmetics and personal care compositions, drug delivery, wound care, hemostasis, industrial paints/coatings, and other uses.

In some embodiments, the polymer or composition is a modified polymer that is amphiphilic. In some embodiments, the polymer is based on a polysaccharide backbone, such as chitosan, alginate, cellulosics, pectins, gellan gums, xanthan gums, dextrans, and hyaluronic acids, among others. In some embodiments, the polymer is a synthetic (i.e., non-natural) polymer, such as polyethylene glycol, polylactic acid, poly-glycolic acid, poly lactic co-glycolic acid, poly lactic co-glycolic acid, polymethylmethacrylate, poly F-caprolactone, polyurethane, silicone, among others.

In some embodiments, the polymer is chitosan having a level of deacetylation of from about 40 to about 90%, or from about 50 to about 80%, with from about 10% to about 50% of functional groups occupied by a hydrophobic group. As used herein, the term "mol %" of a hydrophobic group refers to the % of available amines occupied by a hydrophobic group, assuming a level of deacetylation (e.g., in the case of chitosan) of 85%. For example, the modified polymer may have about 5 to about 100 moles of hydrophobic group per mole of polymer. The molecular weight of the polymer is from about 40,000 to about 500,000 Daltons.

The polymer may have from 2 to about 10 different hydrophobic groups, and optionally from 2 to about 5 different hydrophobic groups (e.g., 2, 3, or 4 different hydrophobic groups). The hydrophobic groups may be independently selected from linear, branched, or cyclic hydrocarbon groups. For example, the hydrophobic groups may include at least one saturated hydrocarbon, which is optionally an acyl group. In some embodiments, the hydrophobic groups include at least one unsaturated, aromatic, or polyaromatic hydrocarbon.

In various embodiments, the hydrophobic groups each have from 1 to about 100 carbon atoms, or from 1 to about 50 carbon atoms. In some embodiments, the hydrophobic groups each have from 1 to about 28 carbon atoms. In some embodiments, the polymer (e.g., chitosan) has at least one or at least two of:

(a) a C1 to C5 hydrocarbon group, which is optionally substituted by non-hydrocarbon moieties;
(b) a C6 to C12 hydrocarbon group, which is optionally substituted with non-hydrocarbon moieties;
(c) a C13 to C28 hydrocarbon group, which is optionally substituted with non-hydrocarbon moieties;
(d) a hydrophobic group having a size greater than C28, which is optionally substituted with non-hydrocarbon moieties. Non-hydrocarbon moieties include heteroatoms or groups comprising heteroatoms such as O, N, S, or halogen.

In some embodiments, the hydrophobic groups comprise C8 hydrocarbon groups, which are present along with at least one of C14, C16, or C18 hydrocarbon groups at a ratio of from 5:1 to 20:1, such as from 5:1 to 15:1, or about 10:1 in some embodiments (C8 to C14/C16/C18).

In some embodiments, the hydrophobic groups comprise C10 or C12 hydrocarbon groups, which are present along with at least one of C14, C16, or C18 hydrocarbon groups at a ratio of from 2:1 to 10:1, such as from 2:1 to 8:1, or about 5:1 in some embodiments (C10/C12 to C14/C16/C18).

In some embodiments, the hydrophobic groups comprise a C1 to C4 hydrocarbon and a C6 to C12 hydrocarbon. In some embodiments, the hydrophobic groups comprise a C6 to C12 hydrocarbon and a C16 to C28 hydrocarbon. In some embodiments, the hydrophobic groups comprise a C1 to C4 hydrocarbon, a C6 to C12 hydrocarbon, and a C16 to C28 hydrocarbon.

In some embodiments, the C1 to C4 hydrocarbon groups (e.g., C1) is present at 5:1 to 25:1 with respect to other larger hydrophobic grafts (e.g., C6 or greater). In some embodiments, C1 to C4 hydrocarbon groups are present at from about 5:1 to about 20:1, or about 5:1 to about 15:1, or about 5:1 to about 10:1 with regard to larger hydrophobic grafts (C6 or greater). In some embodiments, C1 to C4 hydrocarbon groups (e.g., C1) is incorporated into the polymer along with C6 to C12 (e.g., C8 or C10 or C12), and C13 to C28 hydrocarbon groups (e.g., C16 or C18).

The polymer composition may be formulated as a solid, liquid, gel, foam, or putty. For example, the polymer may be a solid, which may be lyophilized or may be a dehydrated solution or dehydrated foam. Thus, the polymer may form a solid matrix. In some embodiments, the polymer is formulated with one or more solvents. The solvents may comprise water. In some embodiments, the solvent comprises an industrial solvent, which may be an organic solvent. In some embodiments, the solvent is paint or industrial coating.

In some embodiments, the modified polymer is present at 0.1 to about 5% by weight in the composition, or in some embodiments, from 0.5 to 2.0% (e.g., about 0.5%, about 1.0%, 1.5%, or about 2%). In some embodiments, the polymer is formulated with at least one synthetic polymer. Exemplary synthetic polymers include polythene, polystyrene, polyacrylate, polyamide, polyester, polyurethane, polysulfide, and polycarbonate. In some embodiments, the synthetic polymer is polyvinyl alcohol.

The modified polymer may provide anti-bacterial and/or anti-fungal properties, which provide unique advantages. For example, the composition may be a fiber or textile as described in PCT/US2017/56887, which is hereby incorporated by reference in its entirety. For example, antimicrobial properties are desirable for many types of garments and fabrics. In some embodiments, the composition is a cosmetic, personal care composition, or drug delivery matrix, as described in WO 2017/177027, which is hereby incorporated by reference in its entirety.

In some embodiments, the composition is paint, industrial coating, or industrial thickener. In such embodiments, the polymer provides unique physical properties to the composition which can provide for improved functionality.

In some embodiments, the composition is a hemostatic device or dressing for bleeding control. There are a myriad of material characteristics that are desired for a well-functioning hemostatic material, including: (1) the material should be easy to apply (ideally flowable to conform to surfaces, cavities, and/or small areas), (2) able to create a rapid seal when in contact with bleeding tissue, (3) retain its mechanical integrity in the face of high pressure bloodflow, (4) be easy to remove, and (5) be safely bioresorbable if left inside the body after use. Traditionally, these attributes are evaluated by mixing a number of different components together (e.g. polymer, nanoparticles, and proteins), due to the assumption that a single material cannot provide all critical characteristics. While a single material that provides tunability in each of these categories would be ideal, such a material is difficult to design, because often chemistries which result in a favorable attribute in one area (e.g. adhesion), result in the detuning of attributes in another area (e.g. cohesion). Here, we describe a framework, utilizing the available chemistry along the chitosan backbone via free amine groups (for example) to create specific hydrophobic designs that employ multiple different grafting lengths and density of hydrophobic groups to achieve optimized properties in flowability, tissue adhesion, cohesion, biodegradation, and removability.

In some embodiments, the modified polymer (e.g., chitosan or other polymer disclosed herein) has both C8 and C18 acyl groups covalently attached to the backbone of the biopolymer, which is both adhesive to tissues, due to the C8 groups, and also cohesive under exudate flow, due the C18 groups. The C8 groups are fluid at room and body temperature, allowing the polymer to spread onto the cell surfaces more effectively, whereas the C18's on neighboring polymer chains hold the polymer molecules together strongly even in the presence of high exudate or blood flow. These embodiments can thus balance adhesive and cohesive properties. Traditional chitosan dressings fail due to either lack of adherence to the wound site or lack of coherence once an initial seal has been achieved. More specifically, native chitosan is particularly good at adhering to wet, bleeding tissue. However, chitosan generally has a limited ability to hold together under high-pressure blood flow.

In accordance with embodiments of the invention, certain hydrophobes provide advantages for optimizing adherence (e.g., to the tissue or wound site), and other hydrophobes are more advantageous for improving coherence (e.g., coherence of the artificial clot). As used herein, the term "artificial clot" refers to physical networks of hydrophobically-modified polymers, blood cells, and surrounding tissue cells which effectively act as a solid barrier to prevent further blood loss. In the range of C6-C12 lengths, the hydrophobic grafts are useful in improving adhesion of the dressings. In the range of C13-C22 lengths, the hydrophobic grafts are useful in improving the cohesion of the dressings. By mixing hydrophobic grafts, for example, C12 and C18 attached to a composition has improved characteristics as compared to native chitosan, 5% C12 chitosan only, or 1% C18 chitosan only. In some embodiments, the polymer has from 1 mol % to 20 mol % C12 hydrophobic groups, or from 2 mol % to about 10 mol % C12 hydrophobic groups, or about 5 mol % C12 hydrophobic groups. In some embodiments, the polymer has from 0.5 mol % to 5 mol % C18 hydrophobic groups, such as from 0.5 mol % to 2 mol % (e.g., about 1 mol %) C18 hydrophobic groups. These may be present for example on medium molecular weight chitosan (MW~250 kDa).

For example, in some embodiments, the hemostat composition is a syringeable gel. The C12 component allows for robust attachment of the gel to the mucosal surface, whereas the C18 component allows for cohesive matrix properties as the blood begins to infiltrate the gel.

In some embodiments, the hemostat composition is a lyophilized sponge. The dressing not only adheres strongly to the bleeding tissue (relative to native chitosan), but also holds together in the presence of significant blood pressure. While a single-length 5 mol % C12 adheres significantly more than native chitosan to wet tissue, it fails upon application of blood pressures much greater than 100 mmHg. Particularly during resuscitation after trauma, there can be a significant risk of re-bleeding at resuscitation pressures.

In some embodiments, the hemostat composition is a clear film. The film not only adheres strongly to the bleeding tissue (relative to native chitosan), but also holds together in the presence of significant blood pressure. While a single-length 5 mol % C12 adheres significantly more than native chitosan to wet tissue, it fails upon application of blood pressures much greater than 30 mmHg. An ability to stand up to such pressures creates an issue in most clinical bleeding scenarios.

In some embodiments, the hemostat composition is a powder. The powder not only adheres strongly to bleeding tissue (relative to native chitosan), but also holds together in the presence of significant blood pressure. While a single-length 5 mol % C12 powder adheres significantly more than native chitosan to wet tissue, it fails upon application of blood pressures much greater than 100 mmHg. Again, during resuscitation after trauma, there can be a significant risk of re-bleeding at resuscitation pressures.

In some embodiments, the hemostat composition is a foam, including a sprayable foam created by mixing the hm-chitosan solution with liquefied gas under pressure in a canister. Upon opening the canister valve to atmospheric pressure, the gas causes rapidly expulsion of the hm-chitosan from the canister. The C12 component of the formulation allows for large expansion of the foam relative to the initial gel volume, whereas the C18 component allows for a mechanically integral final foam product. The foam described herein may also be a syringeable foam, where a double-barrel syringe system connected to a mixing tip is utilized. Gas is released upon mixing the material in one barrel, hm-chitosan dissolved in dilute acetic acid in water, with the material in the other barrel, a neutrally or negatively charged polymer dissolved in water containing a low concentration of sodium bicarbonate. Upon mixing with the acetic acid, the bicarbonate released carbon dioxide gas, causing the foaming and expansion of the hm-chitosan. These and related embodiments are disclosed in PCT/US2018/025742, which is hereby incorporated by reference in its entirety.

In some embodiments, the hemostat composition is a moldable putty. Hydrophobically-modified chitosan in the form of a moldable putty composition is described in U.S. Pat. No. 9,616,088, which is hereby incorporated by reference in its entirety. For example, the gel at 1.0 wt % (in aqueous 0.15 M lactic acid) is thick, but has an ability to mix with polyvinyl alcohol and sodium tetraborate to create a putty-like mechanical characteristic. The C12 component of the formulation allows for robust attachment of the putty to the mucosal surface, whereas the C18 component allows for cohesive matrix properties as the blood begins to infiltrate the putty.

The second component of the putty is a secondary polymer matrix. In a preferred embodiment, the secondary polymer matrix is a polyvinyl alcohol (PVA) in the molecular weight range of 125,000 Da to 140,000 Da. In a further embodiment, the PVA is in the molecular weight range of 50,000 Da to 125,000 Da. In another further embodiment, the PVA is in the molecular weight range of 140,000 Da to 300,000 Da. In such exemplary embodiment, the secondary polymer can be included in concentration of between 5 wt % and 15 wt %. In a preferred embodiment, the level of hydrolysis of the PVA is in a range from 70% to 100% hydrolyzed. In a further embodiment, the level of hydrolysis of the PVA is in a range from 30% to 70%. A crosslinker, sodium tetraborate decahydrate, is included in the blend at a concentration of between 0.1 wt % and 1.0 wt %. The hemostatic polymer, chitosan or hydrophobically-modified chitosan, is included in the putty blend a concentration of between 0.1 wt % and 3 wt %. It is contemplated that the crosslinker may include sodium tetraborate decahydrate, or other borate salts, such as sodium perborate or sodium metaborate.

When a crosslinker is present, the crosslinker interacts with the secondary polymer based upon hydrogen bonding or ionic weak interactions. For example, when borate salts are used as a crosslinker, di-diol interactions with the matrix polymer assist in enhancing the viscoelasticity of the hybrid composition. Such interactions are present in compositions without a crosslinker, but addition of the crosslinker helps enhance these properties. The weak interaction between the polymer chains results in the viscoelastic character of the putty that enables it to conform to highly three-dimensional wounds. Likewise, the viscoelastic character may be tuned by varying polymer molecular weight, polymer concentration, crosslinker type, or concentration of crosslinker.

Alternatively, or in addition, incorporation of small hydrophobic groups, such as C1 to C4 acyl chains, allows the chitosan to degrade more predictably from lysozyme activity in the body. This is very important for creating a material which can be left inside the body after treatment of the wound. More specifically, hydrophobic groups below the length of C6 do not contribute towards improved hemostatic effect. However, hydrophobic modification in the range of C1 to C6 allow for a framework to optimize the degradation of the material inside the body via lysozymes. Particularly in the case of surgical-use hemostats, it is ideal for the hemostatic biomaterial to degrade quickly after achieving hemostasis. For example, 5 mol % C12 and 30 mol % C1 attached to a medium molecular weight chitosan (MW~250 kDa) creates a composition having improved biodegradation characteristics relative to either native chitosan, 5 mol % C12 chitosan only, or 30 mol % C1 chitosan only. Other variations, including with C6 to C12 (e.g., C8 or C10 or C12) and C13 to C28 (e.g., C16 or C18) hydrocarbon groups are described herein. In some embodiments, C1 to C4 acyl chains are incorporated at from 10 mol % to 80 mol %, such as from 10 mol % to 60 mol %. In some embodiments, the C1 to C4 acyl chains are incorporated at 20 mol % to 60 mol %, or from 20 mol % to 50 mol %, or from 20 mol % to 40 mol %.

In some aspects, the invention provides a method for treating a wound, comprising, applying the polymer or composition with hemostatic properties to a bleeding wound. In some embodiments, the wound has high exudate or blood flow. In some embodiments, the polymer composition provides advantages in tissue adhesion as well as material cohesion (for creating a barrier even with high blood flow). In some embodiments, the material degrades in the body within about two months, within about one month, or within about two weeks, or within about one week, or with about two days. In some embodiments, the material is mechanically removable from the wound without damaging the underlying tissue. In various embodiments, the modified polymer (in the amount employed) is soluble in aqueous environment.

In some embodiments, the composition has antimicrobial properties. While the mechanism of action of chitosan as an anti-microbial is a not well understood, two key contributing mechanisms likely play a role: (1) penetration into the bacterial cells and intercalation with plasmid DNA, thus preventing replication, and (2) physical immobilization of cells due to physical binding of bacteria into a robust cohesive network. Smaller hydrophobes (e.g., C1-C12) assist with interfacing with the cell membrane and/or cell wall, and larger hydrophobes (e.g., C13-C22) may assist with physical binding of the bacteria into immobilized networks. Hence, the variable-length design framework, along a wide span of polymer (e.g., chitosan) backbone lengths, allows for the creation of many unique molecules which can amplify a given mechanism towards bacterial death depending upon the clinical circumstances. Certain bacteria are more susceptible to penetration through the cell well (typically gram negative); infections caused robust bacteria may be limited to treatment via molecules that work only by physical bacteriostasis (e.g. multi-drug resistant bacteria).

Figure 2:
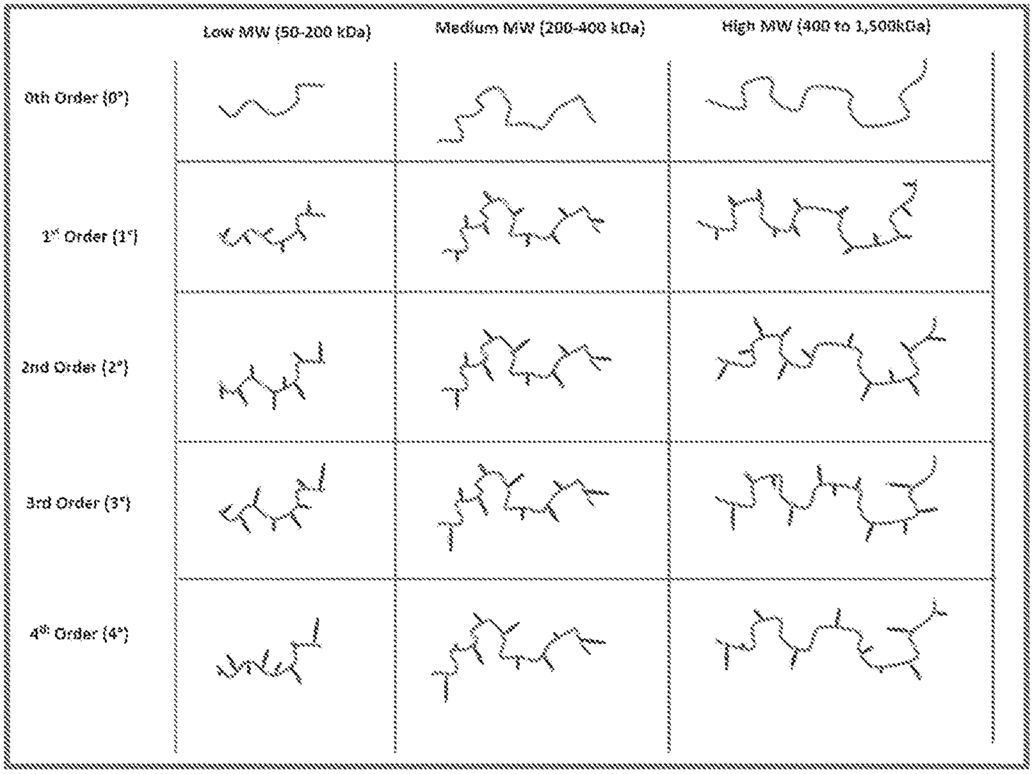
FIG. 2 illustrates variable-sized hydrophobically-modified polymers applied to differently sized polymer backbones.

In some embodiments, and as illustrated in FIG. 1, the polymer composition is a second-order (2nd Order), third-order (3rd Order) or fourth-order (4th Order) hm-polymer, such as a hm-chitosan. Further, and as shown in FIG. 2, the 2nd Order, 3rd Order, or 4th Order biopolymer can be based on a low molecular weight polymer (e.g., 50-200 kDa), a medium molecular weight biopolymer (200-400 kDa), or high molecular weight polymer (400 to 1,500 kDa).

An exemplary hm-polymer material is hm-chitosan. Chitosan is the common name of the linear, random copolymer that consists of β-(1-4)-linked D-glucosamine and N-acetyl-D-glucosamine. The molecular structure of chitosan consists of a linear backbone linked with glycosidic bonds. Chitosan is the major component of crustacean shells such as crab, shrimp, krill and crawfish shells. Additionally, chitosan is the second most abundant natural biopolymer after cellulose. Commercial chitosan samples are typically prepared by chemical de-N-acetylation of chitin under alkaline conditions. Depending on the source of the natural chitin (extracted from shells) and its production process, chitosan can differ in size (average molecular weight Mw) and degree of N-acetylation (% DA). While the poor solubility of chitosan in water and in common organic solvents restricts its applications, reactive amino groups in the chitosan backbone make it possible to chemically conjugate chitosan with various molecules and to modulate its properties for use in textiles.

The degree of deacetylation of chitin may range from about 40-100%, or in some embodiments, from 60 to 100%, which determines the charge density. The structure of chitosan (deacetylated), and is depicted in Formula 1:

Formula 1

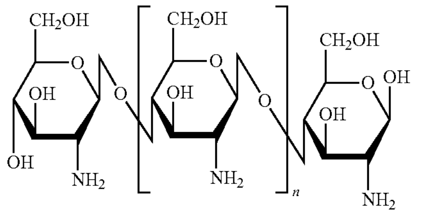

These repeating monomeric units include a free amino group, which makes molecules or compounds containing chitosan or its derivatives readily reactive. The hydrophobic modification of the chitosan backbone is through the association of an amphiphilic compound with the amino group, such that the hydrophobic tail of the amphiphilic compound is bound with the hydrophilic backbone structure.

In some embodiments, the polymer is one or more hm-polysaccharides, including but not limited to cellulosics, chitosans, alginates, pectins, gellan gums, xanthan gums, dextrans, and hyaluronic acids, all of which are abundant, natural biopolymers. In some embodiments, the hm-biopolymer contains cationic groups. hm-chitosan, for example, is a stable, robust, and durable biopolymer which is capable of retaining its functionality for extremely long storage periods at room temperature. The natural origin of these polysaccharides varies; cellulosics are found in plants, whereas chitosans and alginates are found in the exoskeleton or outer membrane of a variety of living organisms. In some embodiments, the hm-chitosan is derived from a deacteylated chitin, which may be derived from one or more of crab, shrimp, krill, and crawfish.

The form of the natural polymers used may vary to include standard states, derivatives and other various formulations. For example, the hm-cellulosics may be formed from, without limitation, hydroxyethyl cellulose, hydroxypropyl cellulose, methyl cellulose, hydroxypropyl methyl cellulose, and/or hydroethyl methyl cellulose. Hm-chitosans may be prepared from, without limitation, the following chitosan salts: chitosan lactate, chitosan salicylate, chitosan pyrrolidone carboxylate, chitosan itaconate, chitosan niacinate, chitosan formate, chitosan acetate, chitosan gallate, chitosan glutamate, chitosan maleate, chitosan aspartate, chitosan glycolate and quaternary amine substituted chitosan and salts thereof. Hm-alginates may be prepared from, without limitation, sodium alginate, potassium alginate, magnesium alginate, calcium alginate, and/or aluminum alginate. It is to be understood that various other forms of any of these natural polysaccharides that provide the proper functional capabilities may be employed without departing from the scope and spirit of the present invention.

In some embodiments, the polymeric component is a mixture of polysaccharides. For instance, the mixture may be of various different sub-classes of a single polymer class. Alternatively, the mixture may include two or more different classes of polymer, for instance a cellolusic and a chitosan, an alginate and a chitosan, and an alginate and a cellulosic.

In various embodiments, the biopolymer is a hm-chitosan, which may be prepared from a chitosan having a degree of deacetylation of from about 40% to about 90%, such as from about 50% to about 80%, such as from about 60% to about 75%. In some embodiments, the degree of substitution of the hydrophobic substituent on the biopolymer (e.g., chitosan) is from about 1 to about 100 moles of the hydrophobic substituent per mole of the biopolymer. In some embodiments, the degree of substitution of the hydrophobic substituent on the polysaccharide is from about 20 to about 100 moles of the substituent per mole of the biopolymer, or from about 40 to about 100 moles of the substituent per mole of the biopolymer, or from about 40 to about 65 moles of the hydrophobic substituent per mole of the biopolymer. In some embodiments, the degree of substitution of the hydrophobic substituent on the biopolymer is from about 1 to about 30 moles of the hydrophobic substituent per mole of the biopolymer (e.g., chitosan). In some embodiments, the molecular weight of the polymer is from about 25,000 to about 1,500,000 grams per mole. In various embodiments, the molecular weight of the biopolymer ranges from about 40,000 to about 500,000 grams per more, or from about 50,000 to about 250,000 grams per mole, or from about 50,000 to about 100,000 grams per mole. As used herein, the term "molecular weight" means weight average molecular weight. Methods for determining average molecular weight of bio-polymers include low angle laser light scattering (LLS) and Size Exclusion Chromatography (SEC). In performing low angle LLS, a dilute solution of the polysaccharide, typically 2% or less, is placed in the path of a monochromatic laser. Light scattered from the sample hits the detector, which is positioned at a low angle relative to the laser source. Fluctuation in scattered light over time is correlated with the average molecular weight of the polysaccharide in solution. In performing SEC measurements, again a dilute solution of biopolymer, typically 2% or less, is injected into a packed column. The polysaccharide is separated based on the size of the dissolved polymer molecules and compared with a series of standards to derive the molecular weight.

A hydrophobically-modified biopolymer material for incorporation into aqueous or organic solutions or suspensions can be based on a solution of the hm-biopolymer that is about 0.1% to about 5.0% by weight relative to the total weight of the composition, or in some embodiments, about 0.5% to about 4%, or about 0.5% to about 3% of the total weight of the composition, or about 0.5% to about 2% of the total weight of the composition. In some embodiments, the biopolymer is about 1.0% to about 5.0% by weight relative to the total weight of the composition of the biopolymer, or in some embodiments, about 1.5% to about 5%, or about 2.0% to about 4% of the total weight of the composition. In some embodiments, the hm-biopolymer solution is dried or lyophilized.

Hydrophobic moieties can be independently selected from saturated hydrocarbons (e.g., alkanes) and unsaturated hydrocarbons (e.g., alkenes, alkynes), which may be linear, branched or cyclic. In some embodiments, the hydrophobic moieties include aromatic hydrocarbons. In some embodiments, the hydrophobic moieties are selected from hydrocarbons having from 1 to about 100 carbon atoms, or from about 1 to about 60 carbon atoms, or from about 1 to about 28 carbon atoms, or from about 1 to about 18 carbon atoms.

The hydrophobic substituents may comprise at least one hydrocarbon group having from about 8 to about 18 carbon atoms attached to the backbone of the one biopolymer, and in some embodiments the C8 to C18 group is an alkyl group. In some embodiments, the hydrocarbon group comprises an arylalkyl group. As used herein, the term "arylalkyl group" means a group containing both aromatic and aliphatic structures.

The modified biopolymer comprises a biopolymer backbone (such as chitosan) that includes a hydrophilically reactive functional group (e.g., amino groups) that binds with the hydrophilically reactive head groups (e.g., carbonyl functional group) of an amphiphilic compound (e.g., aldehyde), to form the hm-chitosan or other hm-polymer. The head group is further associated with a hydrophobic tail group. In the current embodiment, the hydrophobic tail may be, for example, a hydrocarbon. Thus, a hydrophobic tail is associated with the biopolymer backbone providing the hydrophobic modification to the molecule that extends from the backbone and may interact with a surrounding environment in numerous ways, such as through hydrophobic interaction with materials.

Examples of procedures for modifying polymers are as follows.

Alginates can be hydrophobically modified by exchanging their positively charged counterions (e.g. Na+) with tertiary-butyl ammonium (TBA) ions using a sulfonated ion exchange resin. The resulting TBA-alginate is dissolved in dimethylsulfoxide (DMSO) where reaction occurs between alkyl (or aryl) bromides and the carboxylate groups along the alginate backbone. Alginate can also be modified by fatty amine groups (e.g. dodecyl amine), followed by addition of 1-ethyl-3-(3-dimethylaminopropyl)carbodiimide, via EDC coupling.

Cellulosics can be hydrophobically modified by first treating the cellulosic material with a large excess highly basic aqueous solution (e.g. 20 wt % sodium hydroxide in water). The alkali cellulose is then removed from solution and vigorously mixed with an emulsifying solution (for example, oleic acid) containing the reactant, which is an alkyl (or aryl) halide (e.g. dodecyl bromide).

Chitosans can be hydrophobically modified by reaction of alkyl (or aryl) aldehydes with primary amine groups along the chitosan backbone in a 50/50 (v/v) % of aqueous 0.2 M acetic acid and ethanol. After reaction, the resulting Schiff bases, or imine groups, are reduced to stable secondary amines by dropwise addition of the reducing agent sodium cyanoborohydride. Alternatively, fatty acid anhydride chemistry may be used, as described herein.

The degree of substitution of the hydrophobic substituent on the polymer is up to 50% of available functional groups, for example, amines in the case of chitosan. For example, the hydrophobic substituent can be added to from 10 to 50% of available amines, or from 20 to 50% of available amine, or from 30 to 50% of available amines.

In some embodiments, the hydrophobic substituent is derived from an amphiphilic compound, meaning it is composed of a hydrophilic Head group and a hydrophobic Tail group. The Head group binds with the polymer and positions the Tail group to extend from the backbone of the polymer scaffold. This makes the hydrophobic Tail group available for hydrophobic interactions. The Tail group is a hydrocarbon of various forms.

Hydrocarbons that find use in accordance with this disclosure may be classified as saturated hydrocarbons, unsaturated hydrocarbons, and aromatic hydrocarbons. From this basic classification system there exist many derivatives and further types of compounds that build therefrom. For example, numerous and varied compounds include more than one aromatic ring and are generally referred to as polyaromatic hydrocarbons (PAH). In some embodiments, the hydrophobic moiety is aliphatic. Aliphatic compounds, carbon atoms can be joined together in straight chains, branched chains, or rings (in which case they are called alicyclic). They can be joined by single bonds (alkanes), double bonds (alkenes), or triple bonds (alkynes). Besides hydrogen, other elements can be bound to the carbon chain, the most common being oxygen, nitrogen, sulfur, and chlorine. Those of ordinary skill in the art will recognize that other molecules may also be bound to the carbon chains and that compounds of such heteroatomic structure are contemplated as falling within the scope of the current invention.

The hydrophobic tail group of the amphiphilic compound bound to the polymer backbone of the current invention is capable of branching and/or allowing the inclusion of side chains onto its carbon backbone. It may be understood that the strength of the hydrophobic interaction is based upon the available amount of "hydrophobes" that may interact amongst themselves or one another. Thus, it may further promote the hydrophobic effect by increasing the amount of and/or hydrophobic nature of the hydrophobic Tail group that is interacting. For instance, a hydrophobic Tail group, which in its original form may include a hydrocarbon chain, may promote an increase in its hydrophobicity (ability to hydrophobically bond and strength of hydrophobic interaction) by having a hydrophobic side chain attach to one of the carbons of its carbon backbone.

The side chains may be linear chains, aromatic, aliphatic, cyclic, polycyclic, or any various other types of hydrophobic side chains as contemplated by those skilled in the art. Some of the contemplated hydrophobic side chains may include the following.

TABLE 1

| Linear Alkanes | | |
|---|---|---|
| Number of C Atoms | Formula | Common Name |
| 1 | $CH_4$ | Methane |
| 2 | $C_2H_6$ | Ethane |
| 3 | $C_3H_8$ | Propane |
| 4 | $C_4H_{10}$ | n-Butane |
| 5 | $C_5H_{12}$ | n-Pentane |
| 6 | $C_6H_{14}$ | n-Hexane |
| 7 | $C_7H_{16}$ | n-Heptane |
| 8 | $C_8H_{18}$ | n-Octane |
| 9 | $C_9H_{20}$ | n-Nonane |
| 10 | $C_{10}H_{22}$ | n-Decane |
| 11 | $C_{11}H_{24}$ | n-Undecane |
| 12 | $C_{12}H_{26}$ | n-Dodecane |
| 13 | $C_{13}H_{28}$ | n-Trideacane |
| 14 | $C_{14}H_{30}$ | n-Tetradecane |
| 15 | $C_{15}H_{32}$ | n-Pentadecane |
| 16 | $C_{16}H_{34}$ | n-Hexadecane |
| 17 | $C_{17}H_{36}$ | n-Heptadecane |
| 18 | $C_{18}H_{38}$ | n-Octadecane |
| 19 | $C_{19}H_{40}$ | n-Nonadecane |
| 20 | $C_{20}H_{42}$ | n-Eicosane |
| 21 | $C_{21}H_{44}$ | n-Heneicosane |
| 22 | $C_{22}H_{46}$ | n-Docosane |
| 23 | $C_{23}H_{48}$ | n-Tricosane |
| 24 | $C_{24}H_{50}$ | n-Tetracosane |
| 25 | $C_{25}H_{52}$ | n-Pentacosane |
| 26 | $C_{26}H_{54}$ | n-Hexacosane |
| 27 | $C_{27}H_{56}$ | n-Heptacosane |
| 28 | $C_{28}H_{58}$ | n-Octacosane |
| 29 | $C_{29}H_{60}$ | n-Nonacosane |
| 30 | $C_{30}H_{62}$ | n-Triacontane |
| 31 | $C_{31}H_{64}$ | n-Hentraiacontane |
| 32 | $C_{32}H_{66}$ | n-Dotriacontane |
| 33 | $C_{33}H_{68}$ | n-Tritriacontane |
| 34 | $C_{34}H_{70}$ | n-Tetratriacontane |
| 35 | $C_{35}H_{72}$ | n-Pentatriacontane |
| 36 | $C_{36}H_{74}$ | n-Hexatriacontane |
| 37 | $C_{37}H_{76}$ | n-Heptatriacontane |
| 38 | $C_{38}H_{78}$ | n-Octatriacontane |
| 39 | $C_{39}H_{80}$ | n-Nonactriacontane |
| 40 | $C_{40}H_{82}$ | n-Tetracontane |
| 41 | $C_{41}H_{84}$ | n-Hentatetracontane |
| 42 | $C_{42}H_{86}$ | n-Dotetracontane |
| 43 | $C_{43}H_{88}$ | n-Tritetracontane |
| 44 | $C_{44}H_{90}$ | n-Tetratetracontane |
| 45 | $C_{45}H_{92}$ | n-Pentatetracontane |
| 46 | $C_{46}H_{94}$ | n-Hexatetracontane |
| 47 | $C_{47}H_{96}$ | n-Heptatetracontane |
| 48 | $C_{48}H_{98}$ | n-Octatetracontane |
| 49 | $C_{49}H_{100}$ | n-Nonatetracontane |
| 50 | $C_{50}H_{102}$ | n-Pentacontane |
| 51 | $C_{51}H_{104}$ | n-Henpentacontane |
| 52 | $C_{52}H_{106}$ | n-Dopentacontane |
| 53 | $C_{53}H_{108}$ | n-Tripentacontane |
| 54 | $C_{54}H_{110}$ | n-Tetrapentacontane |
| 55 | $C_{55}H_{112}$ | n-Pentapentacontane |
| 56 | $C_{56}H_{114}$ | n-Hexapentacontane |
| 57 | $C_{57}H_{116}$ | n-Heptapentacontane |
| 58 | $C_{58}H_{118}$ | n-Octapentacontane |
| 59 | $C_{59}H_{120}$ | n-Nonapentacontane |
| 60 | $C_{60}H_{122}$ | n-Hexacontane |
| 61 | $C_{61}H_{124}$ | n-Henhexacontane |
| 62 | $C_{62}H_{126}$ | n-Dohexacontane |
| 63 | $C_{63}H_{128}$ | n-Trihexacontane |
| 64 | $C_{64}H_{130}$ | n-Tetrahexacontane |
| 65 | $C_{65}H_{132}$ | n-Pentahexacontane |
| 66 | $C_{66}H_{134}$ | n-Hexahexacontane |
| 67 | $C_{67}H_{136}$ | n-Heptahexacontane |
| 68 | $C_{68}H_{138}$ | n-Octahexacontane |
| 69 | $C_{69}H_{140}$ | n-Nonahexacontane |
| 70 | $C_{70}H_{142}$ | n-Heptacontane |
| 71 | $C_{71}H_{144}$ | n-Henheptacontane |
| 72 | $C_{72}H_{146}$ | n-Doheptacontane |
| 73 | $C_{73}H_{148}$ | n-Triheptacontane |
| 74 | $C_{74}H_{150}$ | n-Tetraheptacontane |
| 75 | $C_{75}H_{152}$ | n-Pentaheptacontane |

TABLE 1-continued

| Linear Alkanes | | |
|---|---|---|
| Number of C Atoms | Formula | Common Name |
| 76 | $C_{76}H_{154}$ | n-Hexaheptacontane |
| 77 | $C_{77}H_{156}$ | n-Heptaheptacontane |
| 78 | $C_{78}H_{158}$ | n-Octaheptacontane |
| 79 | $C_{79}H_{160}$ | n-Nonaheptacontane |
| 80 | $C_{80}H_{162}$ | n-Otcacontane |
| 81 | $C_{81}H_{164}$ | n-Henoctacontane |
| 82 | $C_{82}H_{166}$ | n-Dooctacontane |
| 83 | $C_{83}H_{168}$ | n-Trioctacontane |
| 84 | $C_{84}H_{170}$ | n-Tetraoctacontane |
| 85 | $C_{85}H_{172}$ | n-Pentaoctacontane |
| 86 | $C_{86}H_{174}$ | n-Hexaoctacontane |
| 87 | $C_{87}H_{176}$ | n-Heptaoctacontane |
| 88 | $C_{88}H_{178}$ | n-Octaoctacontane |
| 89 | $C_{89}H_{180}$ | n-Nonaoctacontane |
| 90 | $C_{90}H_{182}$ | n-Nonacontane |
| 91 | $C_{91}H_{184}$ | n-Hennonacontane |
| 92 | $C_{92}H_{186}$ | n-Dononacontane |
| 93 | $C_{93}H_{188}$ | n-Trinonacontane |
| 94 | $C_{94}H_{190}$ | n-Tetranonacontane |
| 95 | $C_{95}H_{192}$ | n-Pentanonacontane |
| 96 | $C_{96}H_{194}$ | n-Hexanonacontane |
| 97 | $C_{97}H_{196}$ | n-Heptanonacontane |
| 98 | $C_{98}H_{198}$ | n-Octanonacontane |
| 99 | $C_{99}H2_{00}$ | n-Nonanonacontane |
| 100 | $C_{100}H_{202}$ | n-Hectane |
| 101 | $C_{101}H_{204}$ | n-Henihectane |
| 102 | $C_{102}H_{206}$ | n-Dohectane |
| 103 | $C_{103}H_{208}$ | n-Trihectane |
| 104 | $C_{104}H_{210}$ | n-Tetrahectane |
| 105 | $C_{105}H_{212}$ | n-Pentahectane |
| 106 | $C_{106}H_{214}$ | n-Hexahectane |
| 107 | $C_{107}H_{216}$ | n-Heptahectane |
| 108 | $C_{108}H_{218}$ | n-Octahectane |
| 109 | $C_{109}H_{220}$ | n-Nonahectane |
| 110 | $C_{110}H_{222}$ | n-Decahectane |
| 111 | $C_{111}H_{224}$ | n-Undecahectane |

II. Cyclic Compounds a. Alicyclic Compound/Cycloalkane/Cycloalkene: An organic compound that is both aliphatic and cyclic with or without side chains attached. Typically include one or more all-carbon rings (may be saturated or unsaturated), but NO aromatic character.

b. Aromatic hydrocarbon/Polycyclic aromatic hydrocarbon/Heterocyclic compound: Organic compounds with a ring structure containing atoms in addition to carbon, such as nitrogen, oxygen, sulfur, chloride, as part of the ring. May be simple aromatic rings, non-aromatic rings. Some examples are pyridine (C5H5N), Pyrimidine (C4H4N2) and Dioxane.

TABLE 2

| Cyclic Compounds | | |
|---|---|---|
| Polycyclic Compounds | Sub-Types | Example Compounds |
| Bridged Compound - compounds which contain interlocking rings | Bicyclo compound | adamantine<br>amantadine<br>biperiden<br>memantine<br>methenamine<br>rimantadine |
| Macrocyclic Compounds | Calixarene<br>Crown Compounds<br>Cyclodextrins<br>Cycloparaffins<br>Ethers, Cyclic<br>Lactans, macrocyclic | |

TABLE 2-continued

| Cyclic Compounds | | |
|---|---|---|
| Polycyclic Compounds | Sub-Types | Example Compounds |
| | Macrolides<br>Peptides, Cyclic<br>Tetrapyrroles<br>Trichothecenes | |
| Polycyclic Hydrocarbons, Aromatic. | Acenaphthenes<br>Anthracenes<br>Azulenes<br>Benz(a)anthracenes<br>Benzocycloheptenes<br>Fluorenes<br>Indenes<br>Naphthalenes<br>Phenalenes<br>Phenanthrenes<br>Pyrenes<br>Spiro Compounds | |
| Steroids | Androstanes<br>Bile Acids and Salts<br>Bufanolides<br>Cardanolides<br>Cholanes<br>Choestanes<br>Cyclosteroids<br>Estranes<br>Gonanes<br>Homosteroids<br>Hydroxysteroids<br>Ketosteroids<br>Norsteroids<br>Prenanes<br>Secsteroids<br>Spirostans<br>Steroids, Brominated<br>Steroids, Chlorinated<br>Steroids, Fluorinated<br>Steroids, Heterocyclic | |

EXAMPLES

Materials and Methods

Hydrophobic Modification of Chitosan; Synthesizing Hm-Chitosan Using Dodecandoic Anhydride and Palmitic Anhydride The following describes the general method of the creation of variable-length hm-chitosan via anhydride chemistry. Two grams of chitosan was dissolved in 100 mL of 0.2 M acetic acid by stirring for 30 minutes in a beaker covered with aluminum foil. The solution was filtered using a vacuum filter. Once the chitosan solution was poured from the flask into a 600 mL beaker, 100 mL of ethanol was added to the flask gradually and swirled around to remove the remaining chitosan on the sides of the flask. The ethanol and remaining chitosan was poured into the beaker with the rest of the chitosan and the solution was heated to 60° C.; the pH was adjusted to 6.0 by dropwise addition of 0.5 M NaOH. In a separate beaker, 20 mL of ethanol was added to a mixture of dodecanoic anhydride (0.24 g for 5% modification) and palmitic anhydride (0.061 g for the 1% modification); the solution was also heated to 60° C. to fully dissolve the fatty anhydrides, and it was then slowly poured into the chitosan solution. The mixture was stirred for 24 hours under heat and the hm-chitosan was then precipitated from the solution by adding 0.2 M sodium hydroxide dropwise.

Rheology of Blood and Chitosan Solution

An AR2000 advanced rheometer with a cone and plate geometry was used to measure the dynamic viscoelastic properties for the experiments of this disclosure. The cone had a 40 mm diameter with a 2-degree angle. In order to ensure that all the measurements were within the linear viscoelastic regions, first stress amplitude sweeps were performed. After the human blood was drawn into the test tubes with the heparin, a pipette was used to add 1 mL of blood onto the plate of the rheometer. Then 1 mL of the chitosan (or hm-chitosan) solution (or foam) was added to the blood on the plate. Once the solutions were combined, the parameters for the rheometer were set up and the run was started. The cone lowered into contact with the solution and a sinusoidal strain was subjected to the subject with increasing frequency of oscillations. The elastic and viscous moduli were obtained over the frequency range of 0.01 to 10 Hz. Dynamic rheology experiments were performed using unmodified chitosan and variable length hydrophobically-modified chitosans.

Foam Canisters

Variable length hm-chitosan was produced by attaching dodecyl anhydride (5 mol % of available amines) and oleic anhydride (1 mol % of available amines) to the chitosan backbone (using a process similar to that described above). All of the hm-chitosan solutions used contained 1.25% modified chitosan with C-12 tails and either a high or a low concentration C-18 tails in a lactate solution. The hm-chitosan, unmodified, and saline solutions were then loaded into spray canisters with AB-46 propellant and a mixture of propane and butane gas before they were ready for use. The canister was approximately in a 70/30 ratio of solution to propellant, which was used in calculating the ratio of blood and saline to add during testing.

Foam samples were sprayed directly onto the rheometer test plate to a mass of approximately 500 g. The blood tests were all performed using a 1 μg:1 μL ratio of solution (70% of the can mass difference) to heparinized bovine whole blood. The tests using saline were performed by adding 400 μL of 0.9 wt % NaCl solution to the mixture per 500 μL of blood that was added, or by adding 400 μL of saline solution per 500 μL of blood, if blood was to be added (in the case of no blood tests). The tests using α-CD used the same ratio as the saline: 400 μL of 100 μM α-CD in 0.9 wt % NaCl solution were added per 500 μL of blood. After addition of blood or treatment to the foam, the mixture was then stirred using a micropipette tip in order to ensure even distribution of the blood or treatment throughout the foam mixture.

All steady and dynamic rheology was performed on a TA Instruments AR2000 rheometer with a cone and plate geometry of 40 mm diameter and 4° cone angle. All tests were performed at the physiological temperature of 37° C. and using a test gap of 118 μm. A dynamic strain sweep was used to determine the linear viscoelastic region of the sample in order to outline the spectrum for the dynamic frequency test.

Biodegradation

To measure initial degradation rates of material, we measured the viscosity of an aqueous solution of 1 wt % hm-chitosan solution (0.2M acetic acid) exposed to chicken egg lysozyme (1 wt %) after one hour. Before addition of lysozyme, the pH of the hm-chitosan solution was adjusted to 5.5 pH via dropwise addition of NaOH (1.0M) under stirring. The zero-shear viscosity at time=0 was compared to the zero shear viscosity at time=1 h via AR 2000 Stress controlled rheometer. The initial degradation rate is expressed as (Viscosity initial−Viscosity final)/(Viscosity final).

Results

Figure 3:
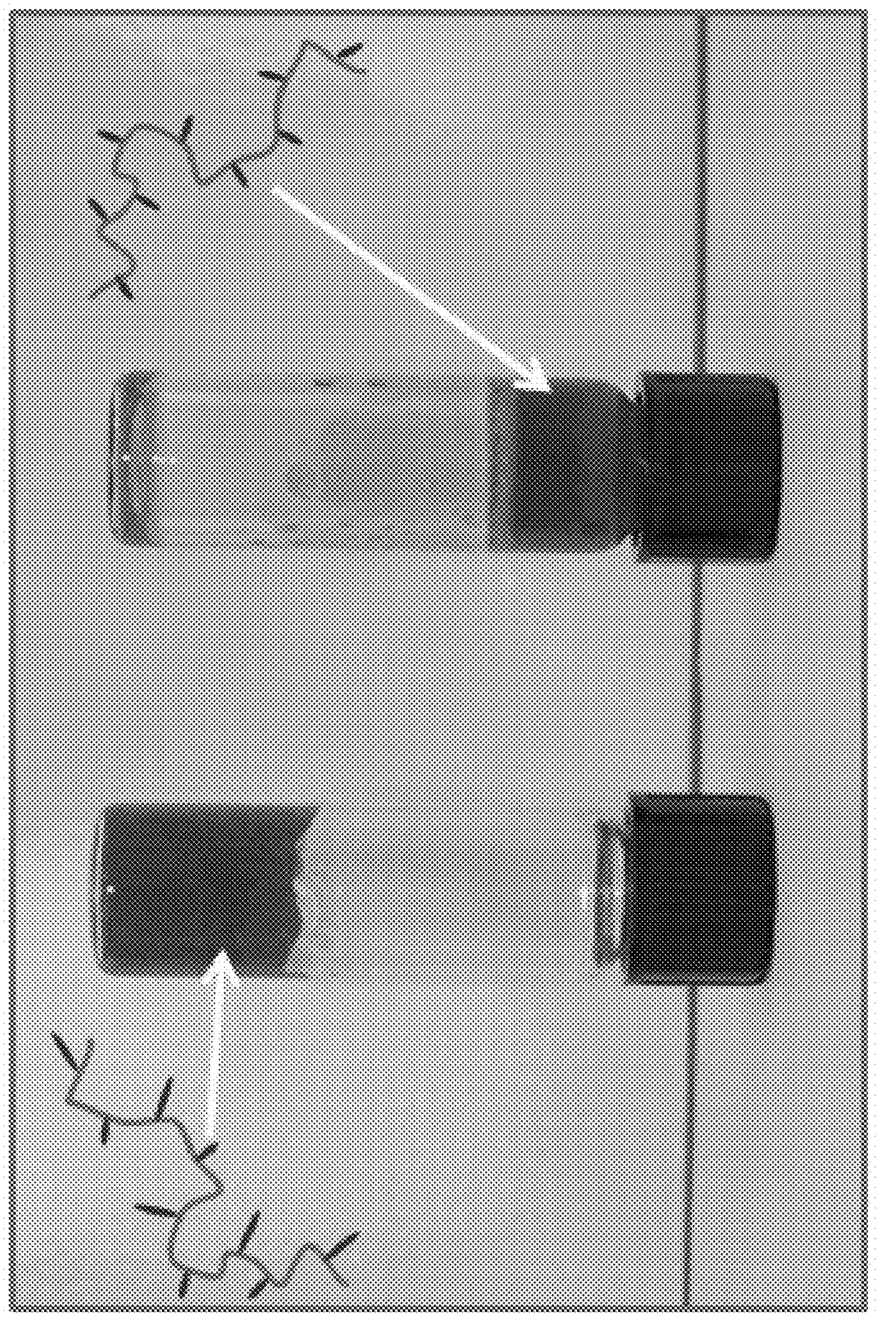
FIG. 3 shows the effect of variable length grafted vs single length grafted hm-chitosan on heparinized bovine blood. (Left) 5 mol % C6, 5 mol % C10 variable length hydrophobically modified chitosan (gel). (Right) 10 mol % C8 single length hydrophobically modified chitosan (flowable). Both polymers have same hydrophobic density, but significantly different gelation properties, highlighting the importance of hydrophobic grafting design with respect to hemostatic or wound treatment functionality.

In FIG. 3, 0.5 mL of a 1.5 wt % solution of modified hm-chitosan was mixed with 0.5 mL of heparinized bovine blood. In the left vial shown in FIG. 3, a variable-length design of 5 mol % C6, 5 mol % C10 variable length hydrophobically modified chitosan was mixed with the blood. The resulting mixture was a gel that holds its own weight upon vial inversion. In the right vial, a 1.5 wt % solution of 10 mol % C8 hydrophobically modified chitosan was mixed with heparinized bovine blood. The native chitosan was a medium molecular weight chitosan (hqg 400 from Primex (Iceland)).

This was a single-length grafting design in this experiment, which had the exact same hydrophobic density as the previously described variable-length composition. However, the gelation properties of the two solutions are distinctly different when mixed with blood. While both polymers have the same hydrophobic density, they have significantly different gelation properties. This is a fundamental example of how variable length designs along the chitosan backbone allow for optimized outcomes with respect to ultimate material handling and performance characteristics. The hydrophobically-modified polymers disclosed herein could be useful as hemostatic biomaterials for treatment of bleeding, from minor oozing in surgeries to severe lacerations in a traumatic event.

Figure 7:
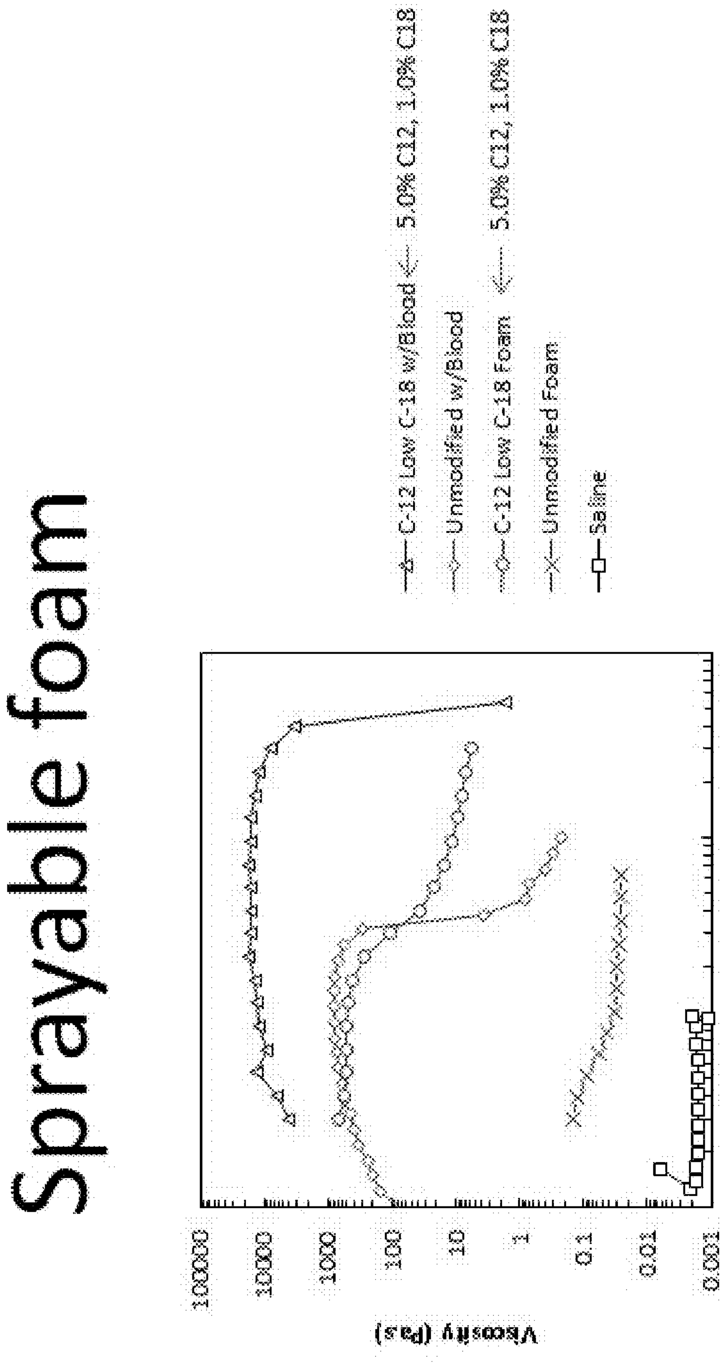
FIG. 7 shows an evaluation of steady shear rheology of hm-chitosan foams. The addition of blood to hm-chitosan (triangles) greatly increases the viscosity over the foam itself (circles). This is apparent for unmodified chitosan as well. The saline foam was also mixed with blood as a control.

Foams (prior to gelling experiment) were compared to gelled foam to ensure that the results of the rheology were because of the gelling of the blood and not a result of the foams initial properties. As shown in FIG. 7, the hm-chitosan foam appears to have some structure prior to the addition of blood. In order to show that the foam structure was not affecting the gelling of the blood, the steady-shear viscosities were compared for both the hm-chitosan (C12 (5 mol %) and C18 (1 mol %) attached) and the unmodified chitosan. FIG. 7 shows that while the modified and unmodified foams (both at initial concentration of 1.25 wt % in the canister) have viscosities greater than that of a saline solution, the addition of blood greatly increases the viscosity because of the gelation of the chitosan polymers.

Figure 8:
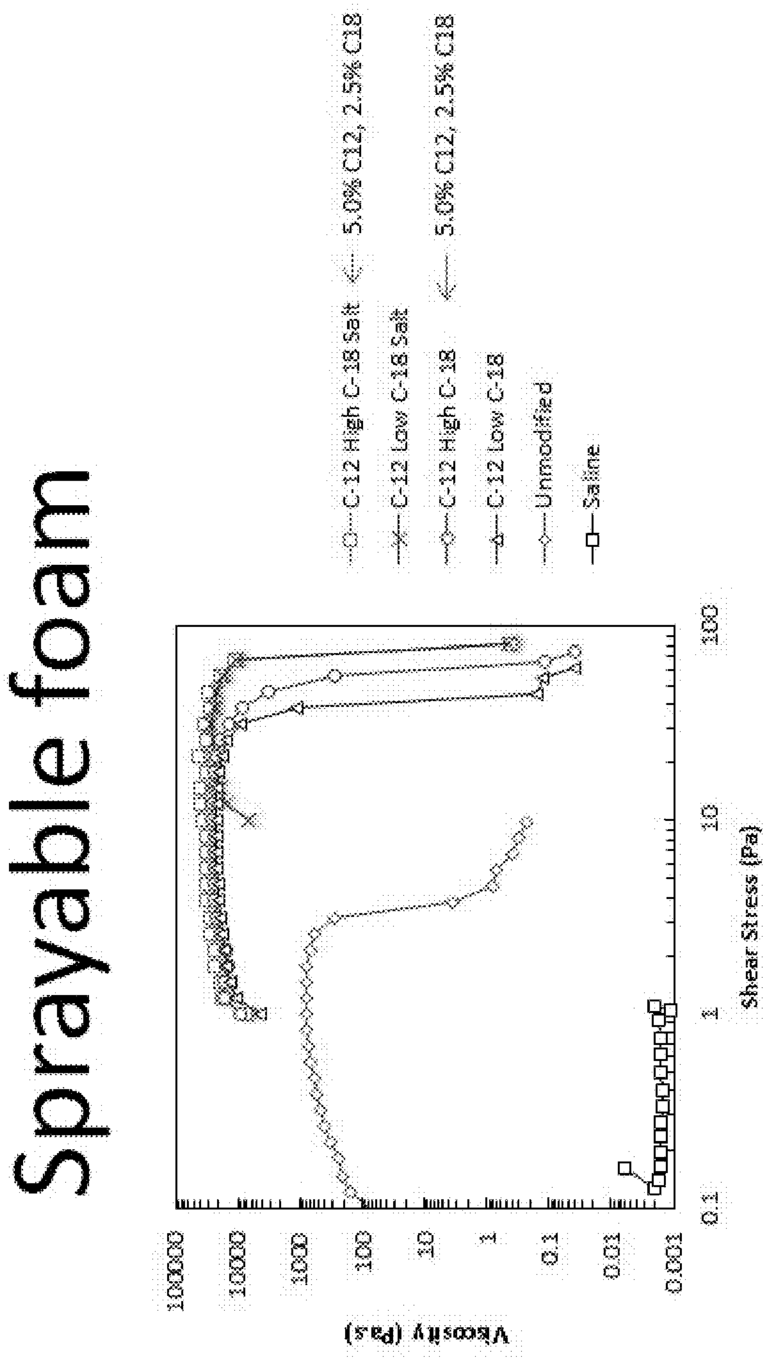
FIG. 8 shows an evaluation of steady shear rheology of hm-chitosan foams, including foams based on low and high molecular weight chitosans.
Figure 9:
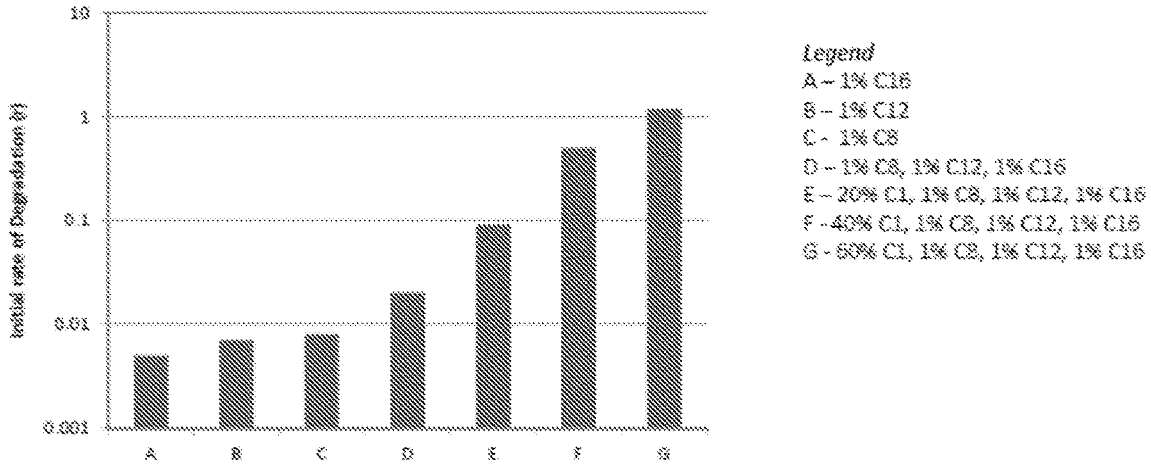
FIG. 9 shows a logarithmic plot of initial degradation rates of chicken egg white lysozyme on hm-chitosans (chitosan backbone is medium molecular weight (Primex hgq 400)). Samples A through G are distinct hydrophobic grafting designs along the chitosan backbone. Samples E, F and G initially degrade much faster due to the presence of large amounts of C1 included in the hydrophobic grafting design.

FIG. 8 also demonstrates how the addition of the variable length hydrophobically modified tails improves the ability of chitosan to gel blood. The addition of hydrophobic tails to the chitosan backbone (C12 (5 mol %) and C18 (2.5 mol %) attached) significantly increased the viscosity and yield stress of the foam and blood mixture. Without the addition of the tails, the chitosan foam was unable to successfully gel the blood, similar to the results of the variable length hm-chitosan solution. Both the chitosan and hm-chitosan had initial concentrations of 1.25 wt % in the canister.

Other preferred multi-variable embodiments for gelation of blood are shown below in Table 3. "%" refers to mol % as described elsewhere herein. All hydrophobic design grafts are attached to a medium molecular weight chitosan (Primex hqg 400). Preferred concentrations of the below variable-length hm-chitosans are 0.1 to 2.5 wt %. Preferred counter-acids are acetic acid, hydrochloric acid, L-lactic acid, citric acid and glutamic acid, each acid concentration being 1 to 2 wt % in water. Grafting of different sizes are randomly distributed along the backbone due to a free reaction of a mixture of fatty anhydrides.

TABLE 3

Exemplary embodiments for blood gelation

| % C6 | % C8 | % C10 | % C12 | % C14 | % C16 | % C18 | Order |
|---|---|---|---|---|---|---|---|
| 5 | | 5 | | | | | 2° |
| | 4 | | 4 | | | | 2° |

TABLE 3-continued

| Exemplary embodiments for blood gelation | | | | | | | |
|---|---|---|---|---|---|---|---|
| % C6 | % C8 | % C10 | % C12 | % C14 | % C16 | % C18 | Order |
| | 10 | | | | 1 | | 2° |
| | | 8 | | | 1 | | 2° |
| | | | 6.5 | | 1 | | 2° |
| | | | 5 | | 1 | | 2° |
| | | | 3 | | 1 | | 2° |
| | 5 | | 2 | | 1 | | 3° |
| | | | 2 | | 1 | | 2° |
| | 1 | | 1 | | 1 | | 3° |
| | | | 5 | | | 1 | 2° |
| | | | 5 | | | 2.5 | 2° |
| | 10 | | 3 | | | 1 | 3° |
| | 1 | | 2 | 1 | | 0.5 | 4° |
| 1 | | 1 | | 2 | | 1 | 4° |

Hydrophobically-modified polymers that balance tissue adhesive properties with material cohesive properties were constructed. In general, biopolymer hemostatic dressings, including chitosan-based dressings, must first adhere quickly and strongly to the site of bleeding in order to create a robust seal. Furthermore, in order to hold back bleeding, the dressings must also be cohesive enough to avoid collapse under high-pressure blood flow. Typically, chitosan dressings fail due to either a lack of adherence to the wound site or a lack of coherence once an initial seal has been achieved. Native chitosan is particularly good at adhering to wet, bleeding tissue. However, native chitosan generally has a limited ability to hold together under high-pressure blood flow.

According to this disclosure, it was discovered that certain hydrophobes are more advantageous for optimizing adherence, and other hydrophobes are more advantageous for improving coherence. For example, in the range of C6-C12 lengths, the hydrophobic grafts are useful in improving adhesion of the chitosan dressing, and in the range of C13-C22 lengths, the hydrophobic grafts are useful in improving the cohesion of the dressings. By mixing hydrophobic grafts, for example in a preferred embodiment of 5 mol % C12 and 1.0 mol % C18 attached to a medium molecular weight chitosan (MW~250 kDa), a composition was created which had improved characteristics compared to either: (1) native chitosan; (2) 5% C12 chitosan only; or (3) 1.0% C18 chitosan only. This composition allowed for the following improvements over a single length hydrophobically modified chitosan:

(A) In a syringeable gel format: A gel was produced at 1.0 wt % solution of variable length modified hm-chitosan (5 mol % C12 and 1.0 mol % C18) (in aqueous 0.15 M lactic acid). This gel was thick, but had flowability through syringe dispensing. The C12 component of the formulation allowed for robust attachment of the gel to the mucosal surface, and the C18 component allowed for cohesive matrix properties as the blood began to infiltrate the gel.

(B) In a lyophilized sponge format: A sponge was created by lyophilizing a 1.0 wt % solution of variable length modified hm-chitosan (5 mol % C12 and 1.0 mol % C18) (in aqueous 0.2M acetic acid) at −40° C. and 50 microbar (pbar), which had a similar look and feel to a native chitosan lyophilized sponge, or a single length hydrophobically modified chitosan sponge. However, when contacted with a bleeding wound, the dressing not only adhered strongly to the bleeding tissue (relative to native chitosan), but also held together even in the presence of significant blood pressure. Thus, while a single-length 5 mol % C12 adheres significantly more than native chitosan to wet tissue, it fails upon application of blood pressures much greater than 100 mmHg. Particularly during resuscitation after trauma, there can be a significant risk of re-bleeding at resuscitation pressures.

(C) In a clear film format: A clear film was created by oven-drying a 1.0 wt % solution of variable length modified hm-chitosan (5 mol % C12 and 1.0 mol % C18) (in aqueous 0.2M acetic acid) at 60° C. and 1 atm, which had a similar look and feel to a native chitosan film, or a single length hydrophobically modified chitosan film. However, when contacted with a bleeding wound, the film not only adhered strongly to the bleeding tissue (relative to native chitosan), but also held together in the presence of significant blood pressure. Thus, while a single-length 5 mol % C12 adheres significantly more than native chitosan to wet tissue, it fails upon application of blood pressures much greater than 30 mmHg. An ability to stand up to such pressures creates an issue in most clinical bleeding scenarios.

(D) In a powderized format: A powder was created by milling a lyophilized sponge produced at 1.0 wt % solution of variable length modified hm-chitosan (5 mol % C12 and 1.0 mol % C18) (in aqueous 0.2M acetic acid) at −40° C. and 50 pbar, which had a similar look and feel to a native chitosan powder, or a single length hydrophobically modified chitosan powder. However, when contacted with a bleeding wound, the powder not only adhered strongly to the bleeding tissue (relative to native chitosan), but also held together in the presence of significant blood pressure. Thus, while a single-length 5 mol % C12 powder adheres significantly more than native chitosan to the wet tissue, it fails upon application of blood pressures much greater than 100 mmHg. Again, during resuscitation after trauma, there can be a significant risk of re-bleeding at resuscitation pressures.

(E) In a sprayable foam format: A sprayable foam was created using a gel at 1.0 wt % solution of variable length modified hm-chitosan (5 mol % C12 and 1.0 mol % C18) (in aqueous 0.15 M lactic acid), which was thick, but had dispensability into an aluminum canister. The canister was then pressurized with a liquefied gas (e.g. isobutene, isopentane, dimethyl ether), and crimped with a valve that allowed the canister to be opened to the atmosphere. The C12 component of the formulations allowed for a large expansion of the foam relative to the initial gel volume, whereas the C18 component allowed for a mechanically integral final foam product.

(F) In an injectable foam format: An injectable foam was created using a gel at 1.0 wt % solution of variable length modified hm-chitosan (5 mol % C12 and 1.0 mol % C18) (in aqueous 0.2 M acetic acid), which was thick, but was fillable into one side of double-barrel syringe. In the other side of the syringe, an aqueous solution of 0.3M sodium bicarbonate. The material in both sides are mixed via a mixing tip, which intakes output from both barrels simultaneously. Upon mixing, carbon dioxide gas is generated due to reaction between the acetic acid and sodium bicarbonate. The C12 component of the formulations allowed for a large expansion of the foam relative to the initial gel volume, whereas the C18 component allowed for a mechanically integral final foam product.

(G) In moldable putty format: The gel at 1.0 wt % solution of variable length modified hm-chitosan (5 mol % C12 and 1.0 mol % C18) (in aqueous 0.15 M lactic acid) was thick, but had an ability to mix with polyvinyl alcohol and sodium tetraborate to create a putty-like mechanical characteristic. The C12 component of the formulations allowed for robust attachment of the putty to the mucosal surface, whereas the C18 component allowed for cohesive matrix properties as the blood began to infiltrate the putty.

In accordance with this disclosure, hydrophobically-modified chitosans were prepared with altered biodegradation profiles. Hydrophobic groups below the length of C6 do not contribute towards improved hemostatic effect of the chitosan polysaccharide. However, hydrophobic modification in the range of C1 to C6 do allow for a framework to optimize the degradation of the material inside the body via lysozymes. Particularly in the case of surgical-use hemostats, it is ideal for the hemostatic biomaterial to degrade quickly after achieving hemostasis.

By mixing hydrophobic grafts, for example in a preferred embodiment of 5% C12 and 30% C1 attached to a medium molecular weight chitosan (MW~250 kDa), a composition was created which had improved biodegradation characteristics relative to either: (1) native chitosan, (2) 5% C12 chitosan only, or (3) 30% C1 chitosan only.

In other embodiments, chitosan-based materials can be useful as anti-microbial agents due to their bacteriostatic effect. While the mechanism of action of chitosan as an anti-microbial is not well understood, two key contributing mechanisms likely play a role: (1) penetration into the bacterial cells and intercalation with plasmid DNA, thus preventing replication; and, (2) physical immobilization of cells due to physical binding of bacteria into a robust cohesive network. Smaller hydrophobes C1-C12 assist with interfacing with the cell membrane and/or cell wall; larger hydrophobes C13-C22 assist with physical binding of the bacteria into immobilized networks. Hence, the variable-length design framework, along a wide span of chitosan backbone lengths, allows for the creation of many unique molecules which can amplify a given mechanism towards bacterial death depending upon the clinical circumstances. Certain bacteria are more susceptible to penetration through the cell wall (typically gram negative); and infections caused by robust bacteria may be limited to treatment via molecules that work only by physical bacteriostasis (e.g. bacteria which have genetically mutated to become resistant to traditional small molecule antibiotic agents).

The invention claimed is:

1. A film composition comprising a hydrophobically-modified chitosan having hydrophobic groups comprising a C1 to C4 hydrocarbon and a C6 to C12 hydrocarbon, wherein the hydrophobic groups are conjugated to the chitosan backbone by fatty acid anhydride chemistry, wherein the hydrophobically-modified chitosan has from about 10% to about 50% of functional groups occupied by a hydrophobic group, wherein the C1 to C4 hydrocarbon groups are incorporated at 20 mol % to 40 mol % with respect to chitosan available amines, and wherein the film is formed from a dried acid solution of the hydrophobically-modified chitosan and a synthetic polymer consisting of polyvinyl alcohol, and wherein the solution is an aqueous solution;

wherein the film is not a viscoelastic composition comprising a cross-linker.

2. The film composition of claim 1, wherein the molecular weight of the chitosan is from about 40,000 to about 500,000 Daltons.

3. The film composition of claim 1, wherein the hydrophobic groups include at least one saturated hydrocarbon.

4. The film composition of claim 1, wherein the hydrophobic groups further comprise a C14, C16, and/or C18 hydrocarbon.

5. A method for treating a wound, comprising, applying the film composition of claim 1 to a bleeding wound.

6. The film composition of claim 1, wherein the acid solution comprises from about 1.0 wt % to about 5.0 wt % of the hydrophobically-modified chitosan.

7. The film composition of claim 1, wherein the hydrophobically-modified chitosan is present in the acid solution at about 0.5 wt % to about 2.0 wt %.

* * * * *